United States Patent [19]

Burkholder et al.

[11] Patent Number: 4,584,193
[45] Date of Patent: Apr. 22, 1986

[54] SYNTHETIC PHEROMONE 5-HYDROXY-4-METHYL-3-HEPTANONE AND ITS USE IN CONTROLLING GRAIN WEEVILS

[75] Inventors: Wendell E. Burkholder; Joel K. Phillips; Catherine A. Walgenbach; Janet A. Klein, all of Madison, Wis.

[73] Assignee: The United States of America as represented by the Secretary of Agriculture, Washington, D.C.

[21] Appl. No.: 716,798

[22] Filed: Mar. 27, 1985

[51] Int. Cl.$^4$ ............................................. A01N 25/00
[52] U.S. Cl. ...................................................... 424/84
[58] Field of Search ........................................... 424/84

[56]  References Cited

U.S. PATENT DOCUMENTS 3,657,414  4/1972  Hedin et al. ........................... 424/84
4,474,755  10/1984  Neal, Jr. et al. ....................... 424/84

OTHER PUBLICATIONS

J. K. Phillips et al., "Evidence for a Male-Produced Aggregation Pheromone in the Rice Weevil," J. Econ. Entomol. 74:539-542 (1981).
C. A. Walgenbach et al., "Male-Produced Aggregation Pheromone of the Maize Weevil, Sitophilus zeamais, and Interspecific Attraction between Three Sitophilus Species," J. Chem. Ecol. 9(7): 831-841 (1983).
D. L. Faustini et al., "Aggregation Pheromone of the Male Granary Weevil, Sitophilus granarius (L.)," J. Chem. Ecol. 8(4): 679-687 (1982).
A. B. Smith et al., "Oxidation of β-Hydroxyketones and Esters: A Convenient Synthesis of 1,3-Diketones and β-Ketoesters," Synthesis, 567-570 (Jul. 1981).
N. R. Schmuff et al., "The Chemical Identification of the Rice Weevil and Maize Weevil Aggregation Pheromone," Tetrahedron Lett. 25(15): 1533-1534 (1984).
C. H. Heathcock et al., "Acyclic Stereoselection. 4. Assignment of Stereostructure to β-Hydroxycarbonyl Compounds by Carbon-13 Nuclear Magnetic Resonance," J. Org. Chem. 44(24): 4294-4299 (1979).
Chemical Abstracts [Index] 91: 210805w and 95:149889r.
J. Econ. Entomol., 74:539-542 (1981).

Primary Examiner—Albert T. Meyers
Assistant Examiner—John M. Kilcoyne
Attorney, Agent, or Firm—M. Howard Silverstein; David G. McConnell; Curtis P. Ribando

[57]  ABSTRACT

The compound 5-hydroxy-4-methyl-3-heptanone (sitophilure) having the structural formula

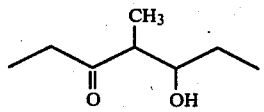

has been identified as an aggregation pheromone for both males and females of grain weevils belonging to the genus Sitophilus. The compound and compositions containing the same are useful tools for the monitoring and control of these major agricultural pests of stored grain.

15 Claims, No Drawings

SYNTHETIC PHEROMONE 5-HYDROXY-4-METHYL-3-HEPTANONE AND ITS USE IN CONTROLLING GRAIN WEEVILS

BACKGROUND OF THE INVENTION

1. Field of the Invention

The genus Sitophilus includes three of the economically important pests of stored grain in the United States. In the adult stage, the grain weevils are responsible for feeding damage to a wide variety of cereal crops. The weevil larvae damage the grain by hollowing the inside of the kernels. The rice weevil, Sitophilus oryzae (L.), is an important grain pest in the American Midwest and South. The maize weevil, S. zeamais Motsch., has a similar distribution and is a strong flier. It is found extensively in the grain growing areas of the South and Southeast. The granary weevil, S. granarius (L)., does not have flight wings and is tolerant of cold temperatures. It is found mainly in the northern grain-growing regions of the U.S.

The continued search for alternatives to the widespread use of insecticides has led to the investigation of pheromones as potential agents for integrated pest management. A number of economically important insects are currently monitored, partially controlled, or completely suppressed by use of their own species-specific pheromones. The previous unavailability of Sitophilus pheromones has precluded application of this technology for the control of grain weevils.

DESCRIPTION OF THE PRIOR ART

The production of the natural aggregation pheromone by a species of Sitophilus was recognized by Phillips et al. [J. Econ. Entomol. 74: 539–542 (1981)]. Paper disks that were exposed to rice weevil males for 1 week, or hexane extracts of the disks, were reported to lure both males and females in a laboratory bioassay. In further studies with the grain weevils, the existence of a granary weevil male-produced aggregation pheromone was reported by Faustini et al. [J. Chem. Ecol. 8: 679–687 (1982)]. Walgenbach et al. [J. Chem. Ecol. 9: 831–841 (1983)] likewise recognized the presence of a male-produced aggregation pheromone in the maize weevil.

SUMMARY OF THE INVENTION

We have now for the first time discovered the identity of a male-produced aggregation pheromone common to the rice weevil and the maize weevil. This pheromone is attractive to both males and females of these two species. It is also attractive to both sexes of the granary weevil, which apparently does not produce the pheromone. This compound, identified as 5-hydroxy-4-methyl-3-heptanone and given the name "sitophilure," has been isolated from young, virgin, male rice and maize weevils, and has also been successfully synthesized. Its usefulness in eliciting a behavioral response when applied to a locus of these weevils suggests two primary economic applications: (1) the monitoring of existing adult populations in order to predict infestation levels for scheduling of treatment with larval insecticides; and (2) the control of reproduction in adult populations either by direct disruption of mating, or by attracting a demographically significant portion of the adult population for subsequent destruction or sterilization.

In accordance with this discovery, it is an object of the invention to identify a unique aggregation pheromone universally attractive to the grain weevils in the genus Sitophilus.

It is also an object of the invention to produce the synthetic counterpart of the natural rice and maize weevil aggregation pheromone.

A further object of the invention is to utilize sitophilure as a monitoring or control agent for economically important species of grain weevils.

Other objects and advantages of this invention will become readily apparent from the ensuing description.

DETAILED DESCRIPTION OF THE INVENTION

The isolation and identification of the aggregation pheromone from the rice and maize weevils is described in detail in Example 1, below.

Sitophilure is characterized by the following structural formula:

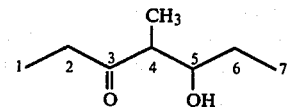

It is apparent therefrom that the compound may exist as any of four stereochemical configurations by virtue of chiral carbons 4 and 5, each accounting for one pair of enantiomers. The four possible configurations are as follows:

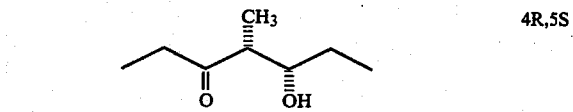

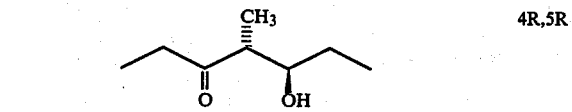

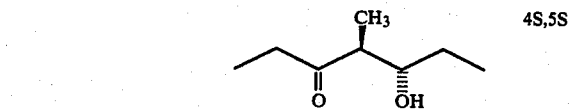

Present bioassay data indicate that the natural pheromonal compound isolated from the rice and maize weevils is the 4S,5R enantiomer. However, we have found that the various enantiomers may be used singly or in any combination for purposes of this invention with the understanding that each species of weevil demonstrates a range of responsiveness to the various individual enantiomers and mixtures thereof.

As previously discussed, the synthetic pheromone may be used as either a monitoring agent or a control agent for adult weevils. In practice, sitophilure is used as a trap bait or is otherwise applied to a locus of the adults in an amount effective to induce an attractant or aggregation response. An effective amount is defined as that quantity of agent which attracts grain weevils to the location of a bait at a rate significantly higher than the weevils are attracted to a nonbaited location. The amount may vary with the species and the enantiomeric constitution, but overall amounts within the range of about 1 ng. to about 10 µg. are effective. Factors such as population density, temperature, wind velocity, and release rate will influence the actual number of weevils trapped. Both sexes of the weevils will respond to the pheromone.

It is envisioned that sitophilure would be effective in monitoring or controlling grain weevil populations when used in conjunction with a trap or pheromone disseminator as known in the art. Typically, the compound would be applied to the device in solution with hexane or other suitable liquid vehicle. The pheromone can also be incorporated into a composition comprising a suitable solid carrier or substrate such as clay, vermiculite, cellulose, grain, resin, or the like. By formulation with an oleaginous extender such as trioctanoin or mineral oil, or by adsorption onto one of the aforementioned substrates or carriers, volatilization of the pheromone can be retarded. The release rate can also be controlled by any of the various encapsulation techniques as known in the art.

The pheromonal composition may be formulated with other agents, particularly those designed to lure or control the weevil populations. For example, we have found that 3-pentanone is attractive to both rice and maize weevils and would therefore serve as an auxiliary attractant. Vegetable oil would likewise have the effect of a secondary attractant and additionally functions as a vehicle for the pheromone. The composition can also be formulated with chemical or biological control agents which would either disrupt mating or have a toxicological effect on the insects.

The following examples are intended only to further illustrate the invention and are not intended to limit the scope of the invention which is defined by the claims.

EXAMPLE 1

Isolation of Natural Pheromone

Pheromone Collection.

Pheromone was obtained by placing 1- or 2-day-old virgin males of rice, maize, or granary weevils individually in clean 1-dr. (15.0×45.0 mm.) vials containing highly absorbent 1.3-cm. diameter paper disks and a single cracked wheat kernel. Two hundred such vials were tightly capped, maintained at standard rearing conditions consisting of a 16:8 light:dark photoperiod, 27±1° C., and 60% ±10% relative humidity. The vials were briefly vented at 2-day intervals to alleviate stress due to lack of oxygen. Control collections contained a disk and cracked grain only; collections from female weevils were handled in the same manner as the male collections. After 14 days, the weevils, grain, and frass were discarded. Disks were then batch extracted in 200 ml. of UV-grade hexane for 24 hr. Glass wool-filtered extracts totalling 2,800 insect day equivalents (IDE) were concentrated under $N_2$ to 0.5 ml., bioassayed to confirm biological activity by the dual choice pitfall method of Phillips et al. [J. Econ. Entomol. 74(5)], herein incorporated by reference, and stored under $N_2$ at −40° C.

Column Chromatography.

Initial purification of disk extracts was accomplished by column chromatography (LC). A 26.0×1.0-cm. (ID) glass analytical column was packed with 60–100/PR "Florisil." The 0.5-ml. volume of crude extract was then applied to the column and eluted isocratically with 1:1 UV-grade hexane-diethyl ether at a flow rate of 1.0 ml./min. Fifty 1.0-ml. fractions of column eluent were collected and later bioassayed to determine which fractions contained pheromone. Two to 7-day-old virgin male and female weevils were tested against paired disks, one spotted with 5.0 µl. of fraction eluent (treatment), and the other with 5.0 µl. of 1:1 hexane-diethyl ether (control). For both male rice and male maize weevil collections, there was an indication of activity in LC fractions 18–33. For granary weevil bioassays, the LC fractions were concentrated (10X) under $N_2$ prior to bioassay. None of the granary weevil LC fractions proved to be attractive. LC fractions were then stored under $N_2$ at −40° C.

Preparative Gas-Liquid Chromatography (GLC).

Isolation of natural pheromone from active 1.0-ml. LC fractions was accomplished by means of preparative GLC. A "Varian 3700" chromatograph, equipped with a flame ionization detector (FID), was fitted with a 1.93-m.×6.35-mm. (ID) stainless steel column packed with 3% "SE-30" on 80/100 mesh "Gas Chrom Q" (column P). A "Scientific Glass Engineering (SGE)" glass-lined, stainless steel, variable effluent splitter was installed to allow glass capillary tube collections of GLC column fractions in a dry ice trap. Biologically active 1.0-ml. LC fractions were concentrated under $N_2$ to 10.0- µl. volumes prior to GLC injection and subsequent pheromone collection. Column conditions during collections were: 50° C. raised to 200° C. at 5° C./min.; injector 150° C.; detector 250° C. During collections, the effluent splitter was completely open, diverting all but a small fraction of the pheromone to the collection tubes. Glass capillary collection tubes were extracted with UV-grade hexane.

Biological Activity.

Bioassays were then conducted on the GLC collections to locate biological activity. Preparative GLC on active LC fractions indicated a peak at 82° C. (6.4 min.) on column P which coincided with biological activity. GLC collections of 2,800 IDE yielded a minimum of ca. 7.5 µg. of pheromone from both the rice and maize weevil collections. Comparisons of preparative GLC peak areas indicated that maize weevil pheromone production was at least four times greater than that of the rice weevil. A biologically active substance with the above GLC retention characteristics was not detectable, for any of the concentrated grain control, female rice or maize weevil, or granary weevil (both sexes) LC fractions. In addition, capillary GLC analyses showed only small peaks at retention times characteristic of the natural pheromone in a 7,100 IDE male granary weevil sample. These peaks suggested the presence of less than 6.0 ng. of pheromone per concentrated granary weevil LC fraction in fractions that corresponded to biologically active rice and maize weevil LC fractions. In contrast, active rice and maize weevil LC fractions often contained microgram quantities of the pheromone.

These purified weevil pheromone fractions were then stored under $N_2$ at −40° C. until tests on the structural features of the pheromone molecule could be conducted. A combination of $^1H$ NMR, gas chromatography-mass spectrometry electron impact analyses, and chemical ionization mass spectra led to the identification of the pheromone as 5-hydroxy-4-methyl-3-heptanone.

EXAMPLE 2

Synthesis of Sitophilure (Method A).

A solution of N,N-diisopropylamine (1.4 ml., 1.1 g., 10.0 mmol.) was prepared in 10.0 ml. of tetrahydrofuran at −78° C. To this solution was added a second solution of n-butyllithium in hexane (6.7 ml., 10.0 mmol.). The resulting solution was immediately allowed to warm to room temperature, then recooled to −60° C. Neat 3-pentanone (1.05 ml., 861.0 mg., 10.0 mmol.) was next added dropwise to the first solution. After maintaining this mixture at −60° C. for 20 min., it was cooled further to −78° C., and neat propionaldehyde (794.0 μl., 639.0 μg., 11.0 mmol.) was added dropwise. After 15 min. at −78° C., the mixture was quenched by the addition of a few ml. of saturated aqueous ammonium chloride. The resultant mixture was then partitioned between 20 ml. of saturated ammonium chloride and 10 ml. of ether. The organic layer was extracted with another 20-ml. portion of ammonium chloride and evaporation of the organic layer in vacuum provided 965 mg. (67%) of a crude, slightly yellow oil. Back extraction of the combined aqueous phases (3×30 ml. of ether) provided another 175 mg. of product (total crude product 1.14 g., 79%). The purity of this product was greater than 90% and the R*S* and R*R* diastereomers were in approximately a 2:1 mixture.

EXAMPLE 3

Synthesis of Sitophilure (Method B).

A 1-liter, 2-necked flask equipped with a dropping funnel, thermometer, and magnetic stirrer was charged with 344.0 g. (4 moles) of freshly distilled 3-pentanone. After cooling the apparatus to 15° C., an addition was made of 30.6 ml. of 16.8% (w/w) potassium hydroxide in methanol. This was followed by dropwise addition over 4 hrs. of 58.0 g. (1 mole) of freshly distilled propionaldehyde mixed with another 172.0-g. lot of 3-pentanone. Stirring was continued for an additional 30 min. after which the base (KOH) was neutralized with 3.5 g. of anhydrous oxalic acid. The solution was filtered and then distilled under vacuum to remove unreacted 3-pentanone and methanol. The aldol distilled at 70° C. (0.45 mm.) and yielded 66.7 g. (46% based on propionaldehyde). The distribution of R*S* and R*R* diastereomers was approximately 1:1.

EXAMPLE 4

"Storgard" traps were used to test the attractive properties of synthetic sitophilure to the rice weevil and maize weevil in a laboratory simulation of a field storage situation. These corrugated cardboard traps housed a plastic cup which contained a 1:1:1 mixture of wheat germ, oat, and mineral oils. Traps also housed rubber septa treated with either sitophilure in hexane or hexane alone. Treatment and control traps were placed in opposite corners of 52×48 cm. stainless steel traps, lined with newsprint to provide the insects with a comfortable walking surface. One hundred insects were held in a glass ring in the center of the test arena for a 30-min. dark conditioning period. The insects were then released, and the number caught in treatment and control traps was recorded 16 hrs. later. Six different doses were examined, and four replicates at each dose level were completed. The results are presented in Table I, below.

TABLE I

Response of Rice Weevil and Maize Weevil to Varying Doses of Synthetic Sitophilure in Combination with Mixed Oils in Cardboard Traps[1]

| Dose level (ng.) | Rice Weevil | | | Maize Weevil | | |
|---|---|---|---|---|---|---|
| | Treatment (T) | Control (C) | T-C | Treatment (T) | Control (C) | T-C |
| 30 | 47.0 | 40.8 | 6.2a | 57.8 | 31.8 | 26.0a |
| 100 | 55.8 | 24.0 | 31.8a,b | 55.8 | 34.0 | 21.8a |
| 300 | 65.8 | 19.3 | 47.5b | 63.5 | 21.5 | 42.0a[2] |
| 1,000 | 64.8 | 19.3 | 45.5b | 58.4 | 26.8 | 31.6a[2] |
| 3,000 | — | — | — | 53.8 | 27.8 | 26.0a |
| 10,000 | — | — | — | 65.0 | 20.2 | 44.8a |

[1]Treatment = synthetic sitophilure; values are means of four replicates; 100 insects/tray; 1 ml. of a 1:1:1 mixture of wheat germ, oat, and mineral oils/trap.
Means in the same column followed by the same letter do not differ significantly ($P>0.05$) according to Ducan's new multiple range test.
[2]Eight replicates.

EXAMPLE 5

Sitophilure, as a 50:50 mixture of R*S* and R*R* diastereomers and of unknown enantiomeric distribution, was bioassayed against maize weevils at five dose levels using the standard dual-choice pitfall bioassay system of Phillips et al., supra. Ten virgin weevils were tested in each of 10 replicate assays. The results are reported in Table II, below.

EXAMPLE 6

Dosages were determined for nearly optimal response of male and female rice, maize, and granary weevils to synthetic sitophilure diastereomers of unknown enantiomeric distribution, or 1:1 mixtures thereof, in the dual choice pitfall bioassay system of Phillips et al., supra. Ten virgin weevils were tested in each of 10 replicate assays. The results are reported in Table III, below.

It is understood that the foregoing detailed description is given merely by way of illustration and that modification and variations may be made therein without departing from the spirit and scope of the invention.

TABLE II

Maize Weevil Response to 50:50 Mixture of R*S* and R*R* Sitophilure

| Dose level (ng.) | Male response, (%)[1] | Female response, (%)[1] |
|---|---|---|
| 1 | 19 (N.S.)[2] | 20 |
| 10 | 54 | 50 |
| 100 | 45 | 43 |
| 1,000 | 53 | 49 |
| 10,000 | 45 | 22 (N.S.)[2] |

[1]Results are reported as the percent of Treatment minus Control (T-C) responding; 10 weevils were tested in each of 10 replicate assays.
[2]N.S. = not significant ($P>0.05$), according to student's t-test for paired data. All other response values highly significant ($P<0.01$).

TABLE III

Grain Weevil Responses to Sitophilure Near Optimum Dose Levels[1]

| Diastereomer | Rice Weevil Dose (ng.) | Response (%)[2] Male | Female | Maize Weevil Dose (ng.) | Response (%)[2] Male | Female | Granary Weevil Dose (ng.) | Response (%)[2] Male | Female |
|---|---|---|---|---|---|---|---|---|---|
| R*S* | 30 | 75.0 | 79.0 | 100 | 76.0 | 58.0 | 400 | 49.0 | 57.0 |
| R*R* | 30 | 75.0 | 73.0 | 400 | 68.0 | 62.0 | 400 | N.S.[4] | N.S.[4] |
| R*S* + R*R* | 30 | 80 | 73.0 | 300 | 78.0 | 58.0 | — | — | — |

[1] Response = number of insects caught in treatment vial in a dual choice pitfall bioassay.
[2] $P > 0.001$; student's t-test for paired data.
[3] $P > 0.01$; student's t-test for paired data.
[4] N.S. = not significant.

We claim:

1. A method of eliciting an attractant or aggregation response in a grain weevil of the genus Sitophilus comprising applying to the locus thereof an effective amount of 5-hydroxy-4-methyl-3-heptanone.

2. A method as described in claim 1 wherein said grain weevil is the rice weevil.

3. A method as described in claim 1 wherein said grain weevil is the maize weevil.

4. A method as described in claim 1 wherein said grain weevil is the granary weevil.

5. A method as described in claim 1 wherein said 5-hydroxy-4-methyl-3-heptanone is in combination with a carrier or vehicle.

6. A method as described in claim 5 wherein said carrier or vehicle is a liquid.

7. A method as described in claim 5 wherein said carrier or vehicle is a solid.

8. An attractant composition comprising the compound 5-hydroxy-4-methyl-3-heptanone in an amount effective to elicit an attractant or aggregation response in a grain weevil of the genus Sitophilus and a carrier or vehicle, wherein said carrier or vehicle has the property of retarding volatilization of said compound.

9. A composition as described in claim 8 wherein said carrier or vehicle is a liquid.

10. A composition as described in claim 8 wherein said carrier or vehicle is a solid.

11. A composition as described in claim 8 wherein said carrier or vehicle is an oleaginous substance.

12. A composition as described in claim 11 wherein said oleaginous substance is selected from the group consisting of trioctanoin, mineral oil, and vegetable oil.

13. A composition as described in claim 11 wherein said oleaginous substance is a vegetable oil.

14. A composition as described in claim 10 wherein said solid carrier or vehicle is selected from the group consisting of clay, vermiculite, cellulose, grain, and resins.

15. An attractant composition consisting essentially of a solution of the compound 5-hydroxy-4-methyl-3-heptanone in an amount effective to elicit an attractant or aggregation response in a grain weevil of the genus Sitophilus, in hexane.

* * * * *